(12) United States Patent
Gregory

(10) Patent No.: US 11,395,684 B2
(45) Date of Patent: Jul. 26, 2022

(54) HEAD TO HEAD CROSS CONNECTOR

(71) Applicant: SPINE WAVE, INC., Shelton, CT (US)

(72) Inventor: Zachary Jordan Gregory, Shelton, CT (US)

(73) Assignee: SPINE WAVE, INC., Shelton, CT (US)

( * ) Notice: Subject to any disclaimer, the term of this patent is extended or adjusted under 35 U.S.C. 154(b) by 197 days.

(21) Appl. No.: 16/570,186

(22) Filed: Sep. 13, 2019

(65) Prior Publication Data
US 2020/0000494 A1  Jan. 2, 2020

Related U.S. Application Data

(62) Division of application No. 15/386,477, filed on Dec. 21, 2016, now Pat. No. 10,413,331.

(51) Int. Cl.
*A61B 17/70* (2006.01)
(52) U.S. Cl.
CPC ...... *A61B 17/7052* (2013.01); *A61B 17/7037* (2013.01); *A61B 17/7008* (2013.01)
(58) Field of Classification Search
CPC ............ A61B 17/7032; A61B 17/7037; A61B 17/7041; A61B 17/7002; A61B 17/7007; A61B 17/701; A61B 17/7038; A61B 17/7049; A61B 17/7011; A61B 17/705; A61B 17/7001; A61B 17/7004; A61B 17/7026
USPC .................................................. 606/250–279
See application file for complete search history.

(56) References Cited

U.S. PATENT DOCUMENTS

| | | |
|---|---|---|
| 5,005,562 A | 4/1991 | Cotrel |
| 5,139,499 A | 8/1992 | Small et al. |
| 5,242,445 A | 9/1993 | Ashman |
| 5,306,275 A | 4/1994 | Bryan |
| 5,380,325 A | 1/1995 | Lahille et al. |
| 5,397,363 A | 3/1995 | Gelbard |
| 5,498,262 A | 3/1996 | Bryan |
| 5,552,816 A | 6/1996 | Dinello et al. |

(Continued)

FOREIGN PATENT DOCUMENTS

| | | |
|---|---|---|
| EP | 0578320 A1 | 12/1994 |
| EP | 0778007 A1 | 6/1997 |
| FR | 2736535 A1 | 1/1997 |

*Primary Examiner* — Eduardo C Robert
*Assistant Examiner* — Tara Rose E Carter
(74) *Attorney, Agent, or Firm* — Hoffmann & Baron, LLP

(57) ABSTRACT

A spinal stabilization system comprises a bone screw including a bone engaging portion and a yoke, the yoke having top surface and bottom surfaces. The yoke has a rod receiving channel defined by a pair of opposed arms, an elongate connecting rod being received within the channel. A head to head cross connector comprises a connecting element having one end in connection with the bone screw and an opposite other end. The one end defines a connecting portion having an opening therethrough and a connecting bar communicating with the opening. The connecting bar, having upper and lower surfaces, resides within the channel, the lower surface contacting the rod. The connecting bar in a non-secured position is movable within the channel in at least two degrees of freedom. A set screw supported by the yoke rigidly secures the connecting bar to the rod and the rod to the yoke.

14 Claims, 7 Drawing Sheets

(56) References Cited

U.S. PATENT DOCUMENTS

| | | |
|---|---|---|
| 5,534,002 A | 7/1996 | Brumfield et al. |
| 5,569,246 A | 10/1996 | Ojima et al. |
| 5,582,612 A | 12/1996 | Lin |
| 5,584,834 A | 12/1996 | Errico et al. |
| 5,662,651 A | 9/1997 | Tornier et al. |
| 5,702,393 A | 12/1997 | Pfaifer |
| 5,873,878 A | 2/1999 | Harms et al. |
| 5,947,966 A | 9/1999 | Drewry et al. |
| 6,171,311 B1 | 1/2001 | Richelsoph |
| 6,217,578 B1 | 4/2001 | Crozet et al. |
| 6,264,658 B1 | 6/2001 | Lee et al. |
| 6,261,287 B1 | 7/2001 | Metz-Stavenhagen |
| 6,283,967 B1 | 9/2001 | Troxell et al. |
| 6,416,515 B1 | 7/2002 | Wagner |
| 6,592,585 B2 | 7/2003 | Lee et al. |
| 6,602,253 B2 | 8/2003 | Richelsoph et al. |
| 6,866,664 B2 | 3/2005 | Schar et al. |
| 6,945,972 B2 | 9/2005 | Frigg et al. |
| 6,958,066 B2 | 10/2005 | Richelsoph et al. |
| 6,960,212 B2 | 11/2005 | Richelsoph et al. |
| 7,029,474 B2 | 4/2006 | Rihelsoph et al. |
| 7,066,938 B2 | 6/2006 | Slivka et al. |
| 7,645,294 B2 | 1/2010 | Kalfas et al. |
| 7,717,939 B2 | 5/2010 | Ludwig et al. |
| 7,722,648 B2 | 5/2010 | Drewry et al. |
| 7,967,845 B2 | 6/2011 | Lauryssen et al. |
| 8,066,743 B2 | 11/2011 | Voung et al. |
| 8,192,471 B2 | 6/2012 | Ludwig et al. |
| 8,197,515 B2 | 6/2012 | Levy et al. |
| 8,246,665 B2 | 8/2012 | Butler et al. |
| 8,262,701 B2 | 9/2012 | Rathbun et al. |
| 8,277,489 B2 | 10/2012 | Saidha et al. |
| 8,353,934 B2 | 1/2013 | Drewry et al. |
| 8,372,120 B2 | 2/2013 | James |
| 8,430,913 B2 | 4/2013 | James et al. |
| 8,454,661 B2 | 6/2013 | Rathbun et al. |
| 8,556,937 B2 | 10/2013 | Ludwig et al. |
| 8,591,550 B2 | 11/2013 | Ludwig et al. |
| 8,672,978 B2 | 3/2014 | Dant et al. |
| 8,784,452 B2 | 7/2014 | Saidha et al. |
| 8,920,469 B2 | 12/2014 | Ludwig et al. |
| 8,920,470 B2 | 12/2014 | Ludwig et al. |
| 8,940,021 B2 | 1/2015 | James |
| 9,023,087 B2 | 5/2015 | Frankel et al. |
| 9,247,964 B1 | 2/2016 | Shoshtaev |
| 9,387,014 B2 | 7/2016 | Ludwig et al. |
| 9,439,684 B2 | 9/2016 | Frankel et al. |
| 9,468,472 B2 | 10/2016 | Barrus et al. |
| 9,486,247 B2 | 11/2016 | Ludwig et al. |
| 2004/0133203 A1* | 7/2004 | Young ............... A61B 17/7052 606/253 |
| 2005/0251141 A1 | 11/2005 | Frigg et al. |
| 2010/0094345 A1* | 4/2010 | Saidha ............... A61B 17/7052 606/250 |
| 2012/0221056 A1* | 8/2012 | Hutton ............... A61B 17/7043 606/264 |
| 2014/0148858 A1 | 5/2014 | Dant et al. |
| 2015/0073482 A1 | 3/2015 | Ludwig et al. |
| 2015/0230830 A1 | 8/2015 | Frankel et al. |
| 2016/0000473 A1 | 1/2016 | Ludwig et al. |
| 2016/0066962 A1 | 3/2016 | Dant et al. |
| 2018/0042647 A1 | 2/2018 | Cowan et al. |

* cited by examiner

HEAD TO HEAD CROSS CONNECTOR

FIELD OF THE INVENTION

The subject invention relates generally to the field of spinal stabilization systems and more particularly to a cross connector that connects to a bone anchor at the juncture of the connection with the longitudinally extending connecting rod.

BACKGROUND OF THE INVENTION

Cross connectors are known to provide transverse rigidity to a dual rod spinal stabilization in a patient. Cross connectors are typically fastened to two parallel connecting rods spanning a length of the spine on opposite contralateral sides of the median plane of the spine. Cross connectors in general can be clumsy to place on the rods in a rod/screw construct, a difficulty that is enhanced by the limited ability to manipulate or position the typical cross connector. For instance, certain cross connectors only permit relative movement of rod-engaging ends towards or apart from each other. In some cases the cross connector may permit relative rotation between the rod-engaging ends within a single plane parallel to the axis of the cross connector. Other cross connector designs allow rotation of a rod-engaging end about its own longitudinal axis.

One known version of a cross connector is used to connect the ends of the cross connector to a portion of the longitudinal connecting rods extending between bone anchors, such as hooks or pedicle screws. An example of this type of cross connector is shown and described in commonly assigned U.S. Pat. No. 8,372,120, entitled "Multi-axial Cross Connector", issued on Feb. 12, 2013 to Anthony James (the '120 patent), the entire contents of which are incorporated herein by reference.

Another type of known cross connector is used to attach to the longitudinal rods at the location where such rods are joined to the bone anchors. This type of cross connector is often considered when the space between bone anchors and hence the extent of the longitudinal connecting rod therebetween is minimal. This condition tends to occur in the cervical spine where vertebrae are smaller than the thoracic or lumber regions of the spine and space for spinal fixations systems is limited. Examples of this type of head to head cross connector are shown and described in U.S. Pat. No. 5,397,363, entitled "Spinal Stabilization Implant System", issued on Mar. 14, 1995 to Gelbard, and U.S. Pat. No. 6,592,585, entitled "Spine Fixing System", issued on Jul. 15, 2003 to Lee et al. Adjustability of these cross connectors is somewhat limited As these systems have evolved, various degrees of freedom of relative orientation were integrated into the systems in order to accommodate misaligned spinal curvature as well as to more flexibility adjust to space limitations as well as anatomic conditions. Advances in head to head cross connectors with improved flexibility and adjustability are shown and described in U.S. Pat. No. 8,672,978, entitled "Transverse Connector", issued on Mar. 18, 2014 to Dant et al., and U.S. Pat. No. 8,784,452, entitled "Transconnector" issued on Jul. 22, 2014 to Saidha et al. While showing improvement in flexibility and adjustability, a drawback of these cross connectors is the increase in height profile at the location of the connection to the bone anchor Nevertheless, there is a need for a head to head cross connector that provides enhanced degrees of freedom to address the wide range of spinal treatment protocols that may be encountered, as well as to provide a relatively low profile at the juncture of the cross connector, bone anchor and connecting rod is a spinal stabilization system.

SUMMARY OF THE INVENTION

It is an object of the invention to provide an improved spinal stabilization system that includes a cross connector that provides multiple degrees of freedom for connecting an elongate connecting rod to a bone screw in the spinal stabilization system.

DESCRIPTION OF THE EMBODIMENTS

Figure 1:
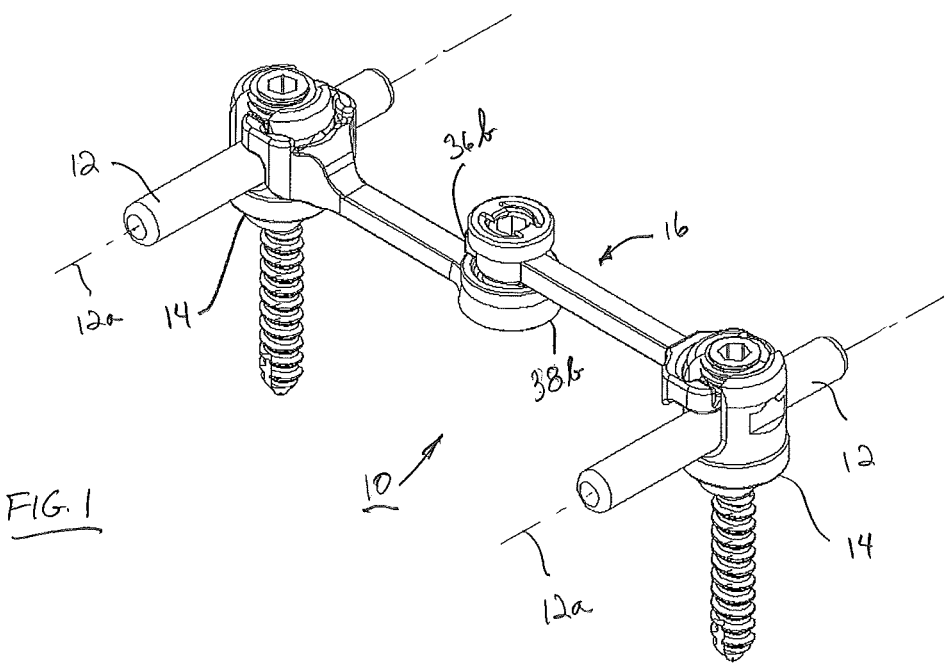
FIG. 1 is a top perspective view of a spinal stabilization system utilizing a head to head cross connector in accordance with an embodiment of the present invention.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
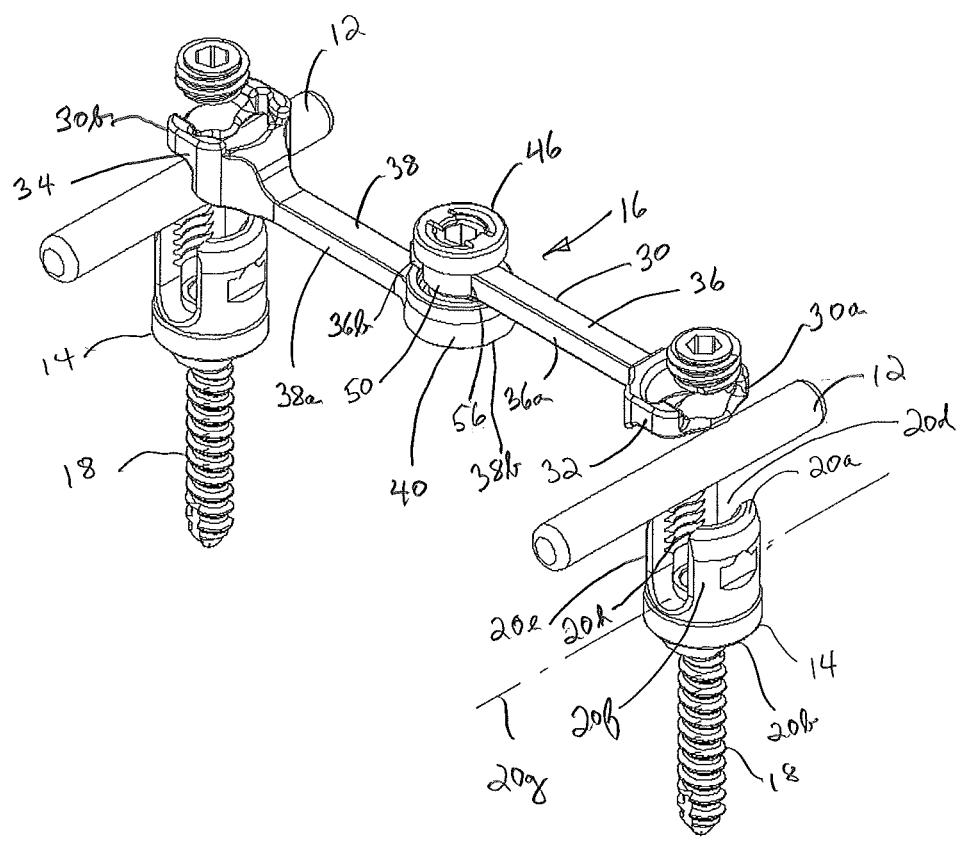
FIG. 2 is an exploded view of the spinal stabilization system of FIG. 1

As shown in FIGS. 1 and 2, a spinal stabilization system 10 spans between successive vertebrae of the spine. A connection member, such as elongate connecting rods 12, each having a longitudinal axis 12a, extends along the length of the spine and provides an anchor point for connecting each vertebra to the system 10. Connecting rods 12, typically formed of stainless steel, are contoured by bending to approximate the normal curvature of the spine for the particular instrumented spinal segments. Bone anchors 14 are provided for connecting each of the vertebral segments to the rods 12 on contralateral sides of the spine. These bone anchors 14 may include hooks, bolts or screws that have bone engaging portions for engaging a vertebra. In a particular arrangement of the present invention, the bone anchor 14 is a bone screw, more specifically, a polyaxial bone screw. Polyaxial bone screw 14 includes features that provide for polyaxial connection to rod 12 in a relatively high degree of angulation. A head to head cross connector 16 is adapted in spinal stabilization system 10 to attach to connecting rods 12 at the location where such rods 12 are joined to the bone screws 14. In a particular example, spinal stabilization system 10 is configured and sized for connection to the cervico-thoracic spine although use in the thoracic and lumbar spine regions is also contemplated.

Figure 3:
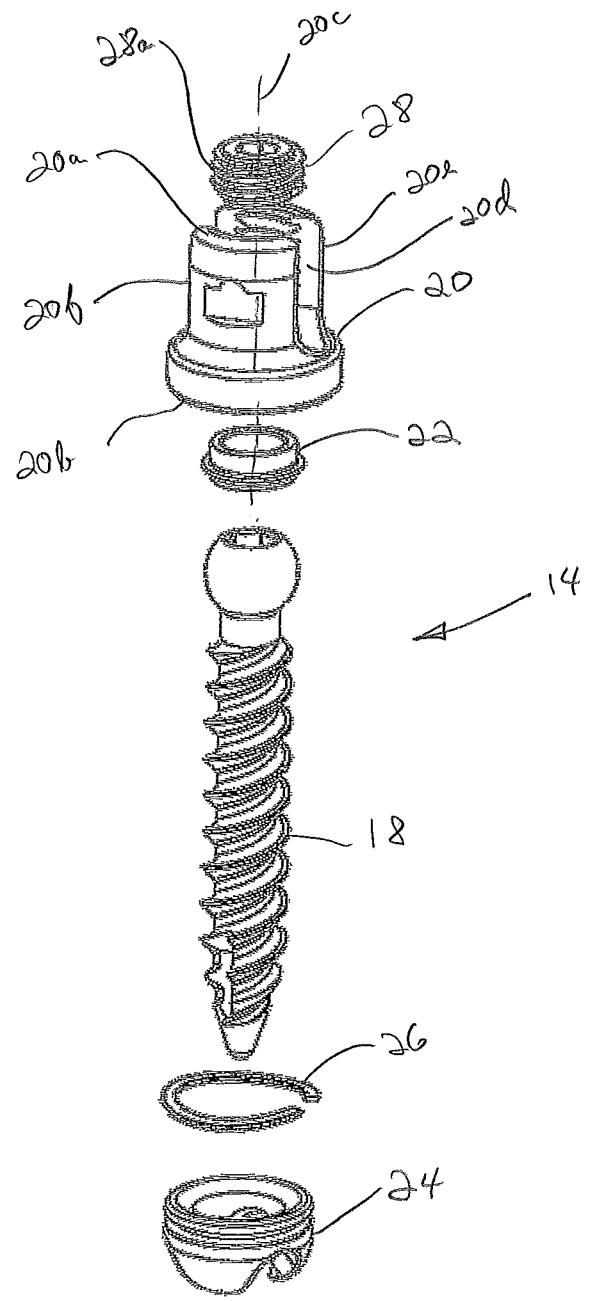
FIG. 3 is an exploded view of the polyaxial bone screw used in the spinal stabilization system of FIG. 1.
Figure 5:
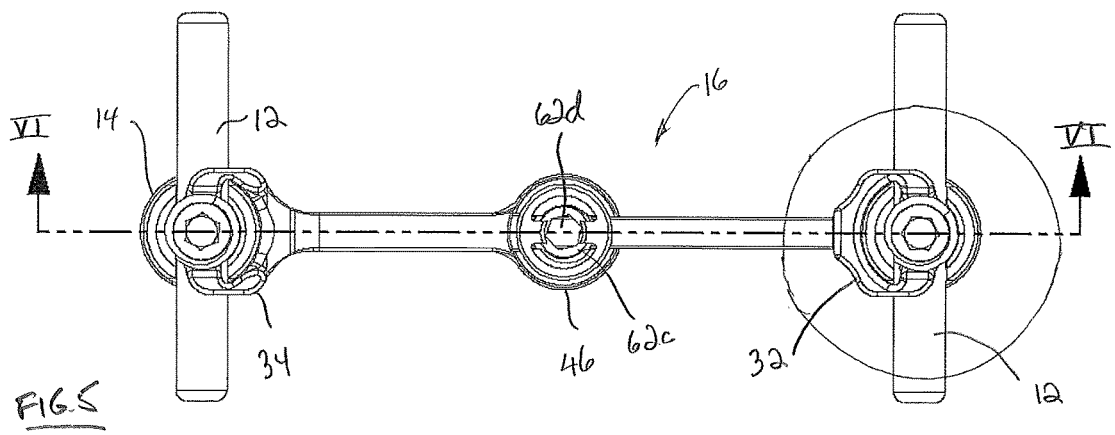
FIG. 5 is a top plan view of the spinal stabilization system of FIG. 1.
Figure 4:
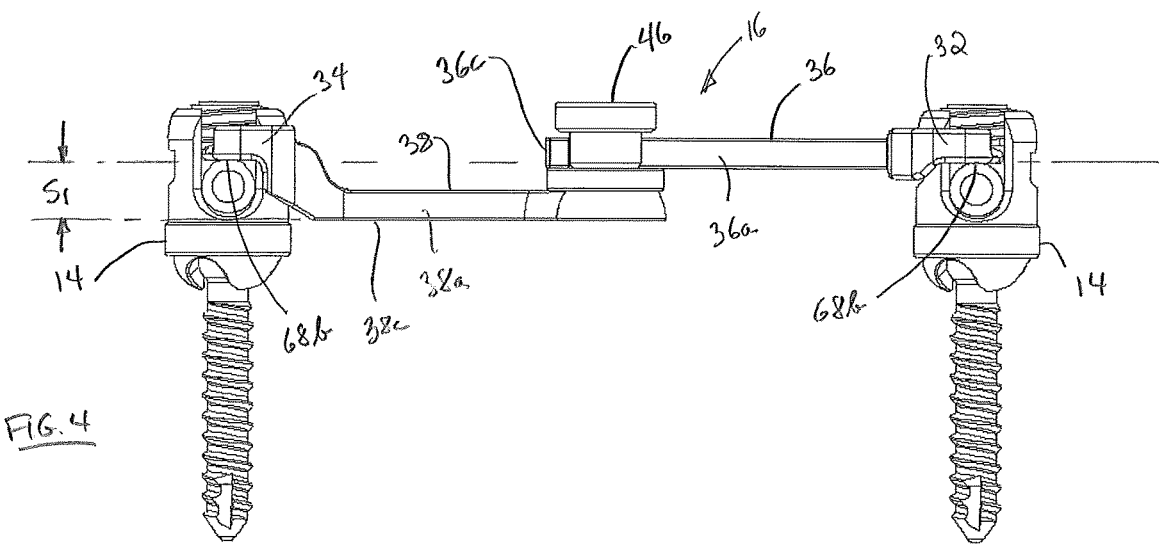
FIG. 4 is an end elevation view of the spinal stabilization system of FIG. 1.
Figure 6:
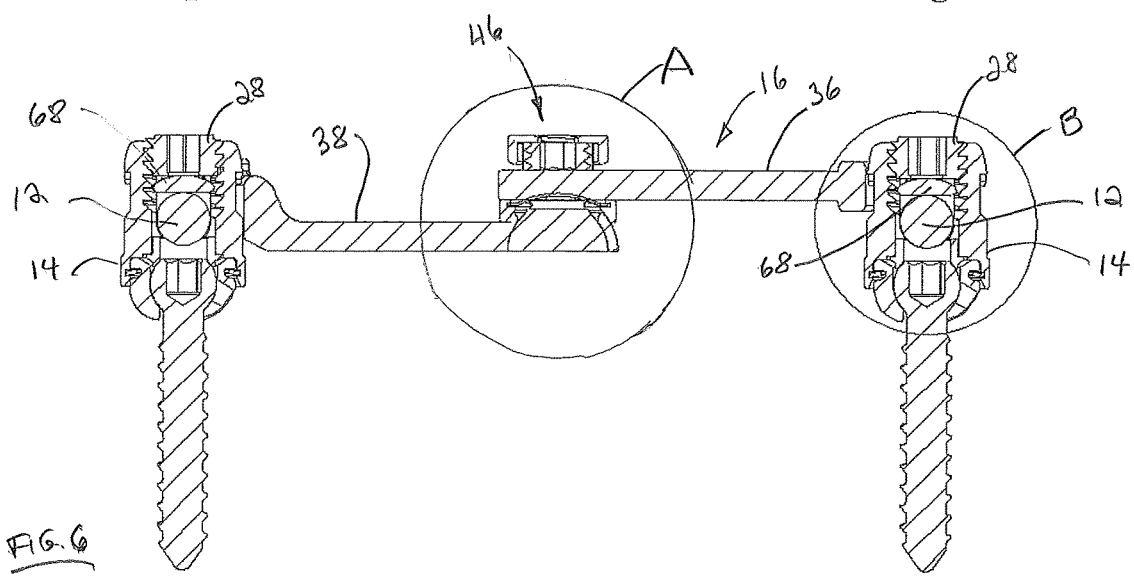
FIG. 6 is a cross-sectional view of the spinal stabilization system as seen along viewing lines VI-VI FIG. 5.

Referring now to FIG. 3, the elements of polyaxial bone screw 14 are shown in exploded view. Polyaxial bone screw 14 comprises a threaded fastener 18 defining a bone engaging portion, a yoke 20, a crown 22, a screw support 24, a connecting element 26 for rotatably connecting screw support 24 and yoke 20, and a fastening element 28. Yoke 20 has a top surface 20a and a bottom surface 20b and a yoke axis 20c extending through top surface 20a and bottom surface 20b. Yoke 20 has a connecting rod receiving channel 20d defined by a pair of opposed upstanding arms 20e and 20f. Channel 20d is generally U-shaped defining a channel axis 20g (see FIG. 2) and extending through yoke top surface 20a. Bone engaging portion 18 projects downwardly from yoke bottom surface 20b. Interior surfaces 20h of arms 20e and 20f are threaded to threadably receive the external threads 28a of fastening element 28, which may be a set screw. Polyaxial bone screw 14 is more particularly described in commonly assigned U.S. patent application Ser. No. 15/378,521 entitled "Polyaxial Bone Screw", filed on Dec. 14, 2016, the entire contents of which are incorporated herein by reference. It should be appreciated that other polyaxial bone screws that include a yoke supporting a threaded bone engaging portion for rotational and articulating movement relative to the yoke may also be used. In addition, monolithic bone anchors, such as pedicle screws or hooks may also be used in the context of the subject invention where less system flexibility and fewer degrees of freedom of component movement within the spinal stabilization system may be tolerated.

Figure 7:
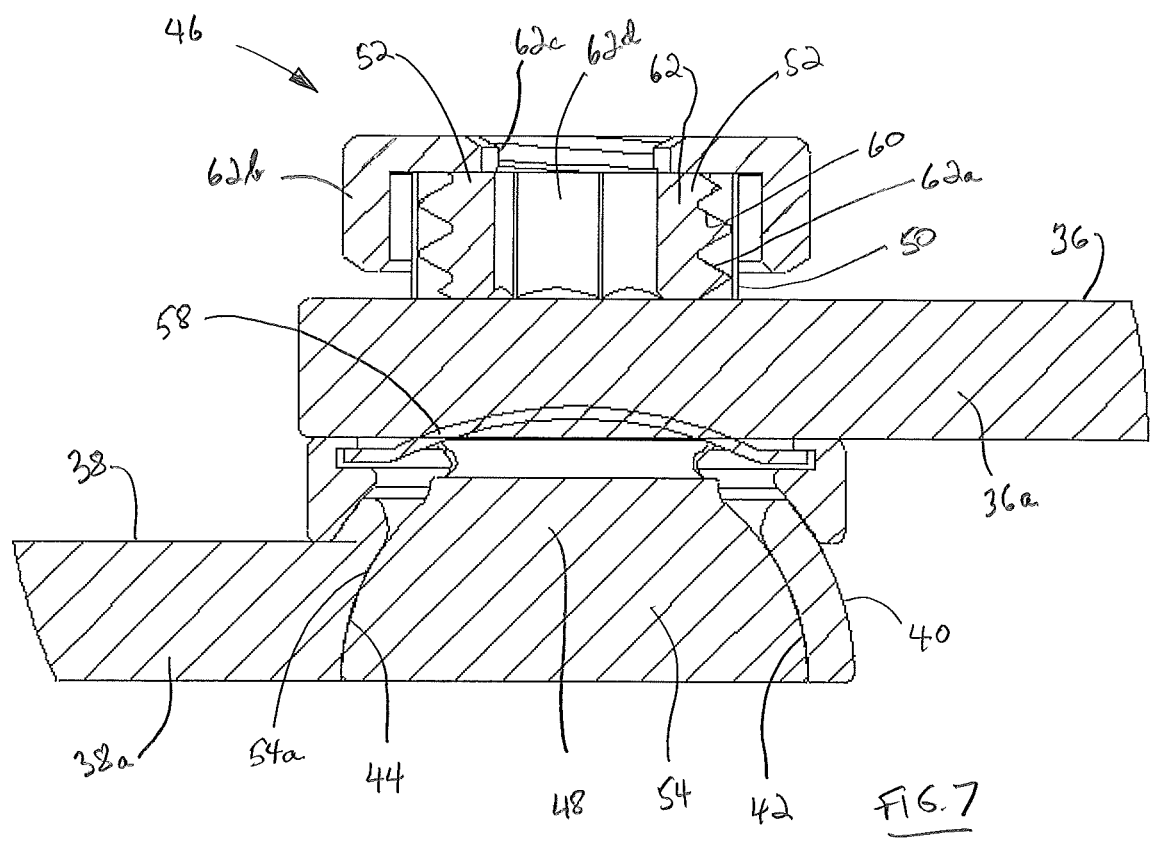
FIG. 7 is an enlarged view of the portion of FIG. 6 within circle A.

Turning now also to FIGS. 4-7, details of head to head cross connector 16 are described. Cross connector 16 includes an elongate connecting element 30 of extent to span the lateral distance between contralateral bone screws 14. Connecting element 30 comprises one end 30a defining a connecting portion 32 for connection to bone screw 14 and an opposite other end 30b defining a connecting portion 34 for connection to a bone screw 14 on the contralateral side of the spine. Elongate element 30 comprises a first "adjustable" element 36 and a second "stationary" element 38. For the purposes of the present description, the designation of one element as being "adjustable" and the other as "stationary" is arbitrary, with the understanding that the intent is to describe that the two elements 36 and 38 are movable relative to each other, as will be described. An elongate bar 36a extends axially from one end 30a of first adjustable element 36 and terminates in an opposite first coupling end 36b. An elongated bar 38a extends axially from other end 30b of second stationary element 38 and terminates in an opposite second coupling end 38b defined by a flange 40. Flange 40 is cup-like and defines an opening 42 extending therethrough as best seen in FIG. 7. An inner surface 44 of flange 40 is spherical to form an annular spherical interface capable of allowing articulation or pivoting in multiple degrees of freedom or about multiple separate axes, as will be described. While elongate bars 36a and 38a are shown as being generally linear, it should be appreciated that elongate bars 36a and 38a and he also be curved.

An adjustment mechanism 46 couples first coupling end 36b and said second coupling end 38b of connecting element 30. Adjustment mechanism 46, the details of which are illustrated in FIG. 7, includes in one embodiment a pivot element 48 defined at its upper portion by a yoke element 50 that includes two opposing branches 52 projecting upward from a base 54 at the lower portion of the pivot element 48. Branches 52 extend through opening 42 in the flange 40 of stationary element 38 and define a slot 56 (see FIG. 3) therebetween that is sized to receive the elongate bar 36a of first adjustable element 36. The bar end 36c of the adjustable element 36 is preferably sized larger than elongate bar 36a so that it cannot pass through the slot 56 when elongate bar 36a is received within the slot 56 to thus prevent disengagement of the two cross connector elements 36, 38 when the elements are moved apart. An upper outer surface 54a of the base 54 is a partially spherical bearing surface forming an articulating joint with the spherical inner bearing surface 44 of the flange 40. It can be appreciated that the yoke element 50 can swivel or pivot in multiple directions or degrees of freedom, or about at least three independent axes, relative to the flange 40 so that the branches 52 of yoke element 50 can be oriented at a range of angles relative to the bar 38a of the stationary element 38.

Adjustment mechanism 46 includes a spring 58 that contacts the elongate bar 36a of first element 36. Spring 58 is calibrated to provide some resistance or friction to hold the cross connector 16 in a particular orientation while permitting continued articulation or pivoting of first element 36 relative to second element 38 until the first and second elements 36, 38 are finally rigidly locked.

Branches 52 of yoke element 50 extend generally parallel to each other and further define an inner threaded surface 60 for receiving a locking element, such as set screw 62. As shown in FIG. 7, set screw 62 has outer threads 62a that are threaded into the branches 52 to bear against elongate bar 36a of first adjustable element 36. A cap 62b may be provided on the top of set screw 62 to partially surround branches 52 so as to prevent splaying of branches 52 during tightening of set screw 62 into yoke element 50. Cap 62b includes an opening 62c configured to permit access to a socket 62d in set screw 62 by a conventional driving tool to thread set screw 62 to branches 52. Although an inner thread and set screw arrangement is described for locking first element 36 within yoke element 50, other clamping or fixation mechanisms are contemplated. For instance, in lieu of the inner threads 60, yoke element 50 may be provided with exterior threads on the branches 52 that are engaged by an internally threaded nut, rather than the externally threaded set screw 62.

Figure 8:
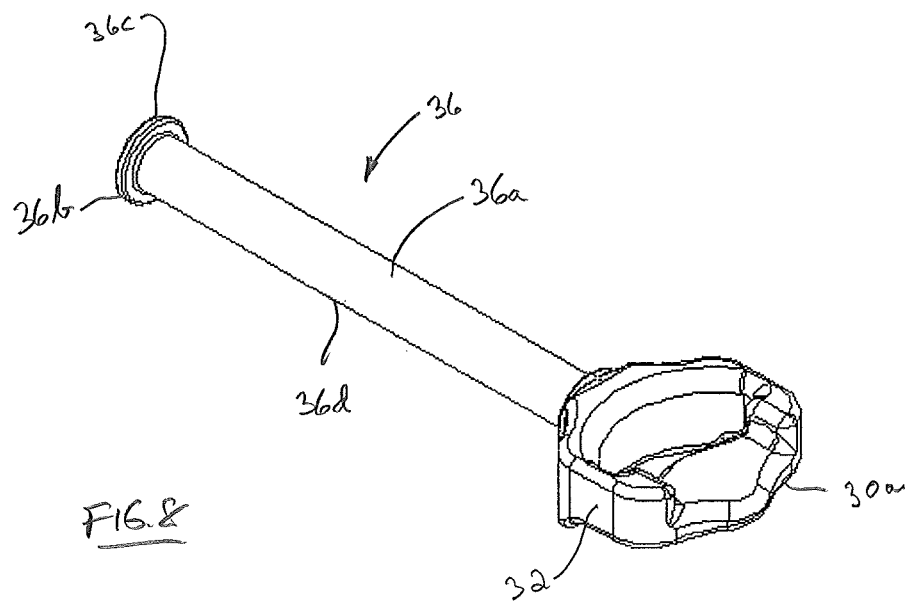
FIG. 8 is a top perspective view an alternative connecting element with a circular rod used in the cross connector of the spinal stabilization system.

Set screw 62 is threaded to branches 52 of the yoke element 50 initially to only loosely retain elongate bar 36a within yoke element slot 56 in a non-locked position. In this position, the spherical interface of adjustment mechanism 46 provided by flange spherical inner surface 44 and yoke base spherical surface 54a permits articulation or pivoting of the two elements 36 and 38 in multiple degrees of freedom or along multiple separate axes. In an addition degree of freedom, first adjustable element 36 may translate axially relative to second stationary element 38 in such non-locked position. In a further degree of freedom as shown in FIG. 8, elongate bar 36a of first adjustable element 36 may formed as a rod 36d having a circular cross-section allowing first adjustable element 36 to also rotate within slot 56 of yoke element 50.

Once the cross connector 16 is arranged in its desired orientation with the respect to bone screws 14, set screw 62 can be fully tightened within the yoke element 50. As set screw 62 is advanced into the inner threaded surface 60 of yoke element 50, the screw 62 pushes the first element 36 downward and pulls the yoke element 50 upward, thereby compressing the first element 36, spring 58 and flange 40 of second element 38 between the set screw 62 and the base 54 of the yoke element 50 to thereby rigidly lock first element 36 and second element 38 in a locked position. Further details of the structure and function of adjustment mechanism 46 are described in the '120 patent, incorporated herein by reference.

Figure 9:
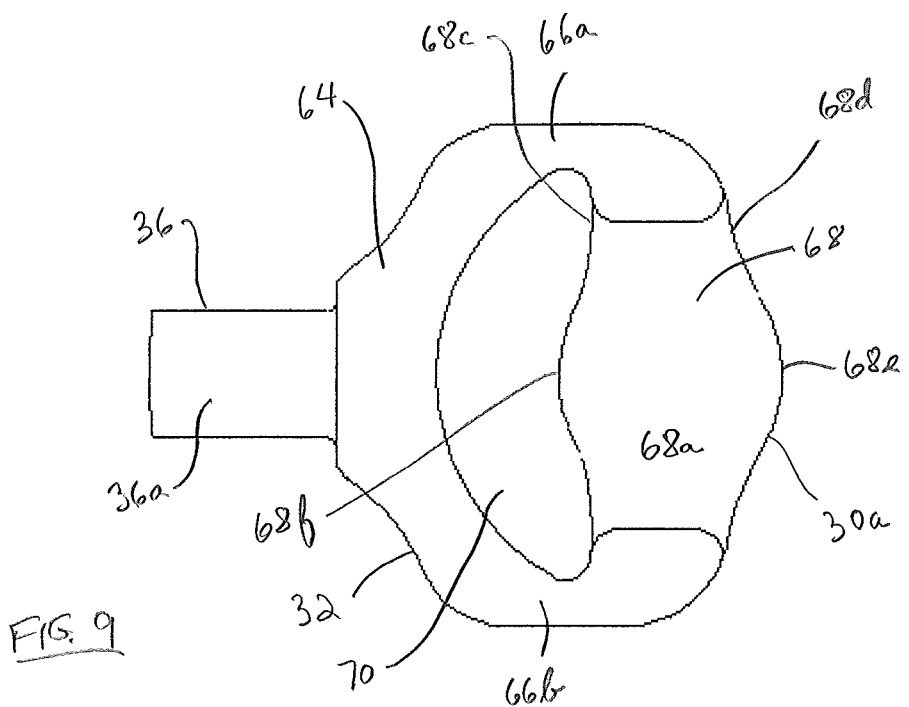
FIG. 9 is an enlarged view of the connecting portion of one of the cross connector connecting elements.
Figure 10:
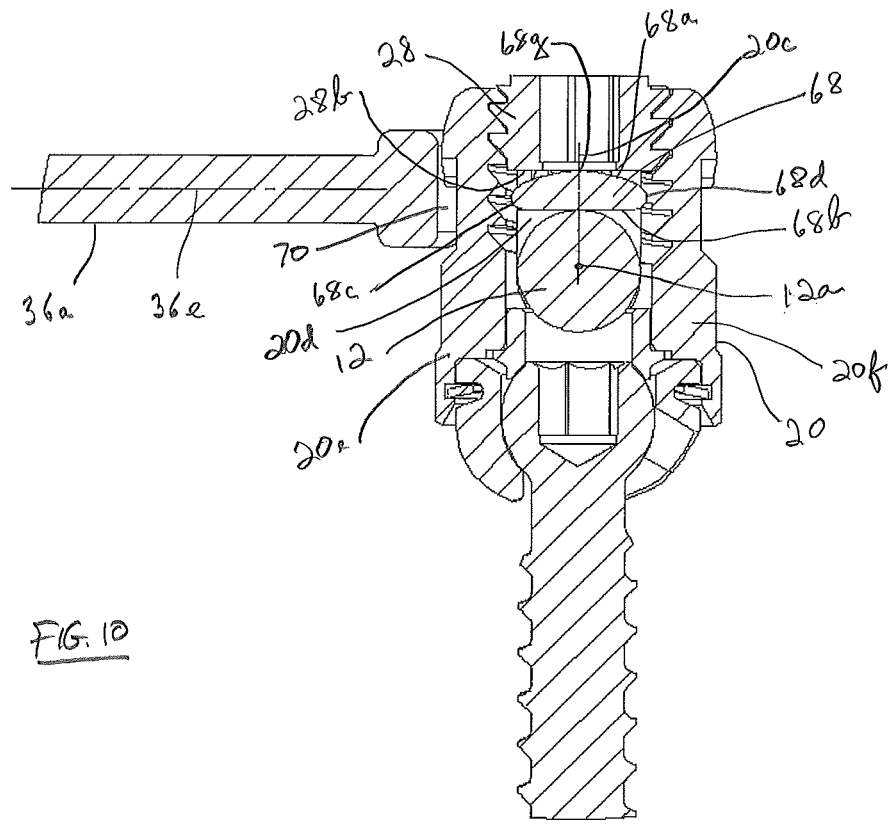
FIG. 10 is an enlarged view of the portion of FIG. 6 within circle B showing one end of the connecting elements of the cross connector in a substantially perpendicular orientation with respect to the bone screw.

Turning now to FIGS. 9 and 10, details of connecting portions 32 and 34 of cross connector 16 are described. In a particular arrangement, connecting portions 32 and 34 are identical, and as such only the details of connecting portion 32 are set forth herein. As seen in FIG. 9, connecting portion 32 includes an enlarged plate 64 at the one end 30a of connecting element 30. Plate 64 comprises a pair of spaced opposing side walls 66a and 66b interconnected by a connecting bar 68. Side walls 66a, 66b, connecting bar 68 and elongate bar 36a define a fully bounded opening 70. Opening 70 is sized and configured to receive one of yoke arms 20e, 20f of bone screw 14 and is formed in a shape to generally mimic the cross-section of one of yoke arms 20e, 20f. In a particular arrangement, opening 70 is generally crescent-shaped, as depicted in FIG. 9. Connecting bar 68 includes an upper surface 68a and a lower surface 68b as shown in FIG. 10, and a pair of spaced opposing side surfaces 68c and 68d extending between upper surface 68a and lower surface 68b. Side surface 68c communicates with opening 70 and side surface 68d defines a terminal end of connecting element 30. Upper surface 68a of connecting bar is formed to have a convexly curved surface while lower surface 68b is formed to have a substantially flat surface, as illustrated in FIG. 10. In a particular arrangement, side surface 68d may include a protruding portion 68e projecting outwardly therefrom and side surface 68c may have a protruding portion 68f protruding inwardly into opening 70. Protruding portions 68e and 68f are formed to generally conform to the shape of yoke channel 20d and to provide enhanced construct strength.

In use in the stabilization system 10, once the desired angulation of bone screw 14 relative to yoke 18 and the orientation of channel 20d of bone screw yoke 20 are properly achieved, connecting rod 12 may then be introduced into yoke channel 20d for securement to polyaxial bone screw 14. Cross connector 16 in the non-locked position is manipulated by articulating first and connecting elements 36 and 38 relative to each other and/or translating or rotating adjustable first element 36 relative to stationary element 38 so as to place connecting portions 32 and 34 in proper position for connecting to contralateral bone screws 14. Once so positioned, the connecting bar 68 of each connecting portion 32, 34 is placed into yoke channel 20d of respective bone screws 14, as shown in FIGS. 10-11, in a non-secured position as yoke arm 20e is simultaneously received in and through opening 70 of connecting portion 32.

In this non-secured position, lower surface 68b of connecting bar 68 of each connecting portion 32, 34 contacts connecting rod 12 and is capable of allowing movement of connecting elements 36, 38 respectively in at least two degrees of freedom relative to bone screw yoke 20. Such movement is further facilitated while adjustment mechanism 46 of cross connector 16 is in the non-locked position.

Figure 11:
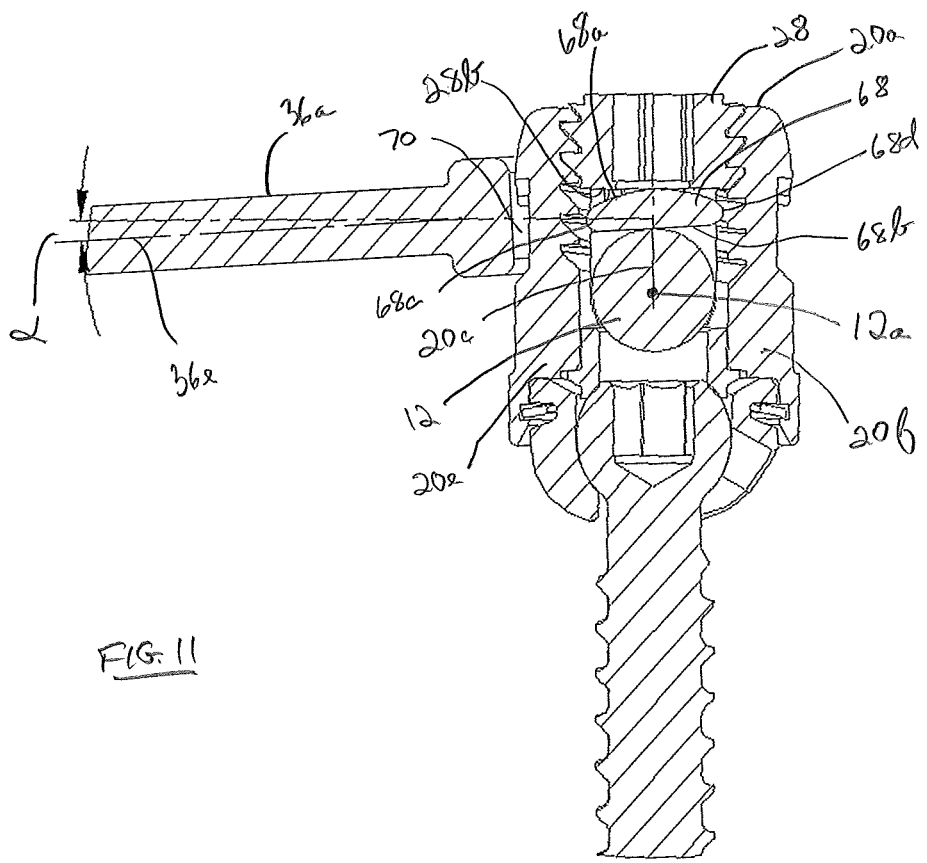
FIG. 11 is an enlarged view of the portion of FIG. 6 within circle B showing one end of the connecting elements of the cross connector in an angular orientation with respect to the bone screw.

In the first degree of freedom as shown in FIGS. 10-11, connecting bar 68 is situated in yoke channel 20d and is sized and configured to move within yoke channel 20d and on the surface of elongate connecting rod 12 about the axis 12a of elongate connecting rod 12. Elongate bar 36a has a longitudinal axis 36e that, as shown in FIG. 10 in one condition, lies substantially perpendicular to axis 20c of yoke 20. Lower surface 68b of connecting bar 68 is in contact with elongate connecting rod 12 and also lies substantially perpendicular to axis 20c. In the adjusted condition shown in FIG. 11, elongate bar 36a, as a result of the movement of connecting bar 68 within yoke channel 20d, is rotated downwardly relative to the perpendicular position of FIG. 10 by an adjustable angle, α. Such movement is facilitated by the curvature of side surfaces 68c and 68d of connecting bar 68, and the substantially flat surface of lower surface 68b of connecting bar 68. As elongate bar 36a is rotated, flat lower surface 68b moves as a tangent on outer surface of connecting rod 12 further enabling rotation of elongate bar 36a relative to yoke 20. It should be appreciated that elongate bar 36a may be similarly rotated upwardly relative to the perpendicular position of FIG. 10. In a particular configuration adjustable angle, α may be about 3° from perpendicular in both directions, thereby establishing a range of adjustment in this first degree of freedom of about 6°. It should also be understood that adjustable angle, α may be increased or decreased by varying the size of opening 70 and/or the width of connecting bar 68, defined by the spacing between side surfaces 68c and 68d.

Figure 12:
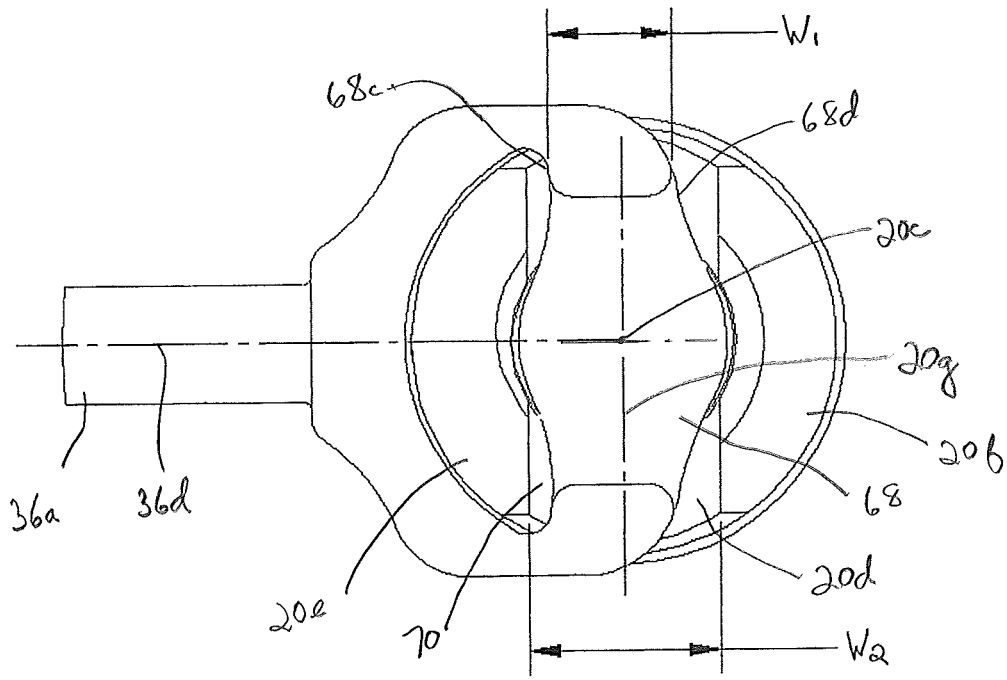
FIG. 12 is an enlarged view of the circled portion of FIG. 5 with the connecting rod removed for clarity showing one end of the connecting elements of the cross connector in a substantially perpendicular orientation with respect to the channel of the bone screw yoke.
Figure 13:
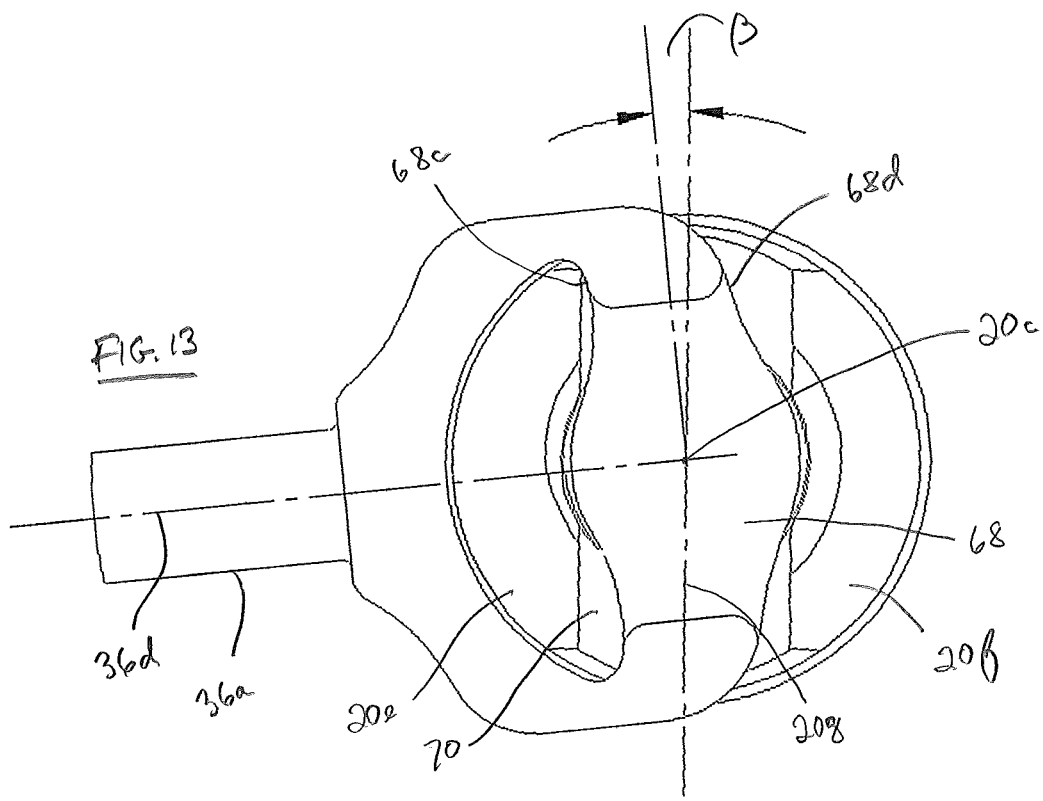
FIG. 13 is an enlarged view of the circled portion of FIG. 5 with the connecting rod removed for clarity showing one end of the connecting elements of the cross connector in an angular orientation with respect to the channel of the bone screw.

In the second degree of freedom as initially illustrated in FIG. 12, connecting bar 68 is situated in yoke channel 20d such that longitudinal axis 36e of elongate bar 36a lies substantially perpendicular to axis 20g of yoke channel 20d. The width $W_1$ of connecting bar 68 is defined by the spacing between side surfaces 68c and 68d. The spacing between yoke arms 20e and 20f adjacent connecting bar side surfaces 68c and 68d defines a channel width, $W_2$. Connecting bar width $W_1$ is formed to be less than channel bar width $W_2$ in an amount sufficient to allow connecting bar 68 to rotate within yoke channel 20d in a second degree of freedom about yoke axis 20c. In the adjusted condition shown in FIG. 13 elongate bar 36a, as a result of the difference between connecting bar width $W_1$ and channel width $W_2$, is rotated about yoke axis 20c relative to the perpendicular position of FIG. 12 by an adjustable angle, β. It should be appreciated that elongate bar 36a may be similarly rotated angularly in an opposite direction relative to the perpendicular position of FIG. 12. In a particular configuration, connecting bar width $W_1$ may be formed to have a dimension of approximately 0.100 inches and channel width $W_2$ may be formed to have a dimension of approximately 0.160 inches with the outer diameter of yoke being approximately 0.354 inches. As such, the ratio of connecting bar width $W_1$ to channel width $W_2$ is approximately 62.5%. In such a configuration adjustable angle, β may be about 6° from perpendicular in both directions, thereby establishing a range of adjustment in this second degree of freedom of about 12°. It should also be understood that adjustable angle, β may be increased or decreased by varying the size of connecting bar width $W_1$ and channel width $W_2$, and hence the ratio of connecting bar width $W_1$ to channel width $W_2$, considering the potential effect on construct strength and desired angulation.

After achieving appropriate orientation of each connecting element 36 and 38 relative to each of the respective contralateral bone screws 14, bone screw fastening element 28, such as a set screw, may then be threaded into yoke 20, by referring again to FIGS. 10-11. In a particular arrangement, the bottom surface 28b a fastening element 28 is formed to have a substantially flat surface. Each set screw 28 is inserted until it loosely contacts upper surface 68a of connecting bar 68 in a manner to allow final manipulation of connecting elements 36 and 38 relative to respective yokes 20. In the event element 36, for example, is in the perpendicular orientation shown in FIG. 10, flat bottom surface 28b of set screw 28 will contact the apex 68g of convexly curved surface 68 as a tangent. In the event element 36 is adjusted by an adjustable angle, α, as shown in FIG. 11, flat bottom surface 28b of set screw 28 will contact upper surface 68a of connecting bar 68 tangentially but at a location between apex 28g and either of side surfaces 68c or 68d. Such tangential contact together with the tangential contact between lower flat surface 68b of connecting bar 68, will allow set screw 28 upon further tightening to apply a uniform compressive force to rigidly secure connecting bar 68 to elongate connecting rod 12 and elongate connecting rod 12 to yoke 20 in a secured position.

Having secured connecting elements 36 and 38 to respective contralateral bone screws 14, coupling ends 36a and 38a of respective connecting elements 36 and 38 may be rigidly locked by adjustment mechanism 46. Set screw 62, as described with reference to FIG. 7, having been loosely placed is then fully tightened within the yoke element 50. As set screw 62 is advanced into the inner threaded surface 60 of yoke element 50, the screw 62 pushes the first element 36 downward and pulls the yoke element 50 upward, thereby compressing the first element 36, spring 58 and flange 40 of second element 38 between the set screw 62 and the base 54 of the yoke element 50 to thereby rigidly lock first element 36 and second element 38 in a locked position. Further details of the structure and function of adjustment mechanism 46 are described in the '120 patent, incorporated herein by reference. Thus, as can be seen in FIGS. 10 and 11 with upper surface 68a of connecting bar 68 being disposed within yoke channel 20d and below yoke top surface 20a, cross connector 16 may be attached at the respective contralateral bone screws 14 with minimal, if any, height added to the profile of the bone screws 14.

While the invention has been illustrated and described in detail in the drawings and foregoing description, the same should be considered as illustrative and not restrictive in character. For example, there may be anatomic conditions wherein it would be desirable for the lower surfaces 68b of respective connecting portions 32 and 34 to lie on substantially the same plane when adjustment mechanism 46 of cross connector 16 is in either the non-locked or locked position. By reference to FIG. 4, it can be seen that first adjustable element 36 is elevated with respect to stationary second element 38 as a result, in part, of the interconnection of elements 36 and 38 at adjustment mechanism 16 where the elongate bars 36a and 38a are in different planes. To allow lower surfaces 68b of each connecting portion 32 and 34 to lie in substantially the same plane 72, a lower surface 68b of connecting portion 34 is offset by a distance S1 from bottom surface 38c of stationary second element 38 in a manner to compensate for the elevation difference at the connection of elements 36 and 38 at adjustment mechanism 46.

It is therefore understood that only the preferred embodiments have been presented and that all changes, modifications and further applications that come within the spirit of the invention are desired to be protected.

What is claimed is:

1. A head to head cross connector for use in a spinal stabilization system that includes a bone anchor having a bone engaging portion and a yoke having a connecting rod receiving channel defined by a pair of opposed upstanding arms, said cross connector comprising:
   a connecting element having one end for connection to said bone anchor and an opposite other end, said one end defining a connecting portion having a fully bounded opening therethrough and a connecting bar communicating with said opening, said opening being sized and configured for receipt therethrough of only one of said arms of said yoke, said connecting bar being sized and configured for receipt in said yoke channel, said connecting bar having a lower surface and an upper surface, said lower surface being substantially flat.

2. The cross connector of claim 1, wherein said upper surface of said connecting bar is convexly curved.

3. The cross connector of claim 1, wherein said connecting bar comprises a pair of spaced opposing side surfaces extending between said upper surface and said lower surface, one of said side surfaces communicating with said opening.

4. The cross connector of claim 3, wherein the other of said side surfaces defines a terminal end of said connecting element.

5. The cross connector of claim 3, wherein at least one of said side surfaces is convexly curved between said upper surface and said lower surface.

6. The cross connector of claim 5, wherein both of said side surfaces are convexly curved between said upper surface and said lower surface.

7. The cross connector of claim 1, wherein said connecting element of said cross connector comprises a first element and a second element, said first element comprising said one end and an opposite first coupling end, said second element comprising said other end of said connecting element and an opposite second coupling end, and wherein said cross connector further comprises an adjustment mechanism coupling said first coupling end and said second coupling end in a non-locked position for movement in at least three degrees of freedom.

8. The cross connector of claim 7, wherein said adjustment mechanism comprises a spherical interface configured to permit articulating movement between said first element and said second element in said non-locked position.

9. The cross connector of claim 8, wherein said first coupling end and said second coupling end are coupled at said adjustment mechanism in said non-locked position to allow relative translational movement between said first element and said second element.

10. The cross connector of claim 9, wherein said first coupling end and said second coupling end are coupled at said adjustment mechanism in said non-locked position to allow relative rotational movement between said first element and said second element.

11. The cross connector of claim 10, wherein said first element is elongate and has a circular cross-section.

12. The system of claim 10, wherein said adjustment mechanism comprises a locking element operative to rigidly lock said first element and said second element in a locked position.

13. The cross connector of claim 12, wherein said opposite other end of said connecting element defines a connecting portion having an opening therethrough and a connecting bar communicating with said opening, said connecting bar having a lower surface and an upper surface, said upper surface being convexly curved.

14. The cross connector of claim 13, wherein said lower surface of said connecting portion of said one end of said connecting element and said lower surface of said connecting portion of said opposite other end of said connecting element lie in said non-locked position in substantially the same plane.

* * * * *